(12) United States Patent
Shukla

(10) Patent No.: US 6,193,991 B1
(45) Date of Patent: Feb. 27, 2001

(54) BIODEGRADABLE DELIVERY SYSTEMS OF BIOLOGICALLY ACTIVE SUBSTANCES

(76) Inventor: Atul J. Shukla, 837 Walnut Bend Rd., Cordova, TN (US) 38018

(*) Notice: Subject to any disclaimer, the term of this patent is extended or adjusted under 35 U.S.C. 154(b) by 0 days.

(21) Appl. No.: 09/181,515

(22) Filed: Oct. 28, 1998

Related U.S. Application Data

(60) Provisional application No. 60/063,680, filed on Oct. 29, 1997.

(51) Int. Cl.[7] .............. A61F 2/00; A61F 13/00; A61K 9/00; A61K 9/22
(52) U.S. Cl. .............. 424/426; 424/423; 424/422; 424/400; 604/890.1
(58) Field of Search .............. 424/426, 423, 424/422, 400; 604/890.1

(56) References Cited

U.S. PATENT DOCUMENTS

| | | |
|---|---|---|
| 4,938,763 | 7/1990 | Dunn et al. . |
| 4,976,962 | * 12/1990 | Bichon et al. .............. 424/424 |
| 5,324,519 | 6/1994 | Dunn et al. . |
| 5,324,520 | 6/1994 | Dunn et al. . |
| 5,340,849 | 8/1994 | Dunn . |
| 5,487,897 | 1/1996 | Polson et al. . |
| 5,632,727 | 5/1997 | Tipton . |
| 5,660,849 | 8/1997 | Polson . |

OTHER PUBLICATIONS

F. Billmeyer, JR., Textbook of Polymer Science, p. 472 John Wiley and Sons, New York, 1984.

Alfred Martin, Physical Pharmacy, p. 588 Lea and Febiger, Philadelphia, 1993.

* cited by examiner

Primary Examiner—Thurman K. Page
Assistant Examiner—Todd D Ware

(57) ABSTRACT

Biodegradable delivery systems of physiologically, pharmacologically and biologically active substance(s) (BAS) are provided. These systems are obtained by incorporating the BAS into a blend of biodegradable polymers and plasticizers using a novel solvent evaporation method. This method involves dissolving the biodegradable polymer or copolymer and a plasticizer into a volatile solvent. The BAS may then be added to this mixture. The volatile solvent is removed using vacuum or at an elevated temperature or using a combination of both vacuum and elevated temperature. The resultant mixture is a BAS-loaded formulation which when injected, implanted or applied in vivo in an animal or human, provides controlled release of the BAS over the desired period of time. Alternatively, a blank formulation may be first prepared by the aforementioned methodology without incorporating the BAS in the formulation. An appropriate quantity of BAS is then added to this formulation to yield a BAS-loaded formulation which may control the release of the BAS for the desired length of time.

22 Claims, 13 Drawing Sheets

FIGURE I

| BIODEGRADABLE POLYMERS | VOLATILE SOLVENTS |
|---|---|
| Polylactic acid (PLA) | Acetone |
| Polylactic-co-glycolic acid (PLGLY) | Ethyl acetate |
| Polyaminoacids | Chloroform |
| Polyhydroxybutyric and | Methyl acetate |
| Valeric acid copolymers (PHBV) | Methylene chloride |
| Poly-ε-caprolatone (PCL) | Methylethyl ketone |
| Lactic acid and caprolactone copolymers | |

↓

SOLUTION OF POLYMER IN VOLATILE SOLVENT(S)
+
PLASTICIZER

Triethyl citrate (TEC), Acetyl triethyl citrate (ATEC), Tributyl citrate (TBC), Acetyl tributyl citrate (ATBC), Glyceryl triacetate (Triacetin), Dimethyl phthalate (DMP), Diethyl phthalate (DEP), dioctyl phthalate, 2-pyrrolidone (2-Pyrrol®), Diethylene glycol monoethyl ether (Transcutol®), n-methyl pyrrolidone (NMP), polyethylene glycols (PEG), PEG-8 glyceryl caprylate/caprate (Labrasol®), propylene carbonate, gamma butyrolactone, dipropylene glycol methyl ether acetate (DPM acetate), vegetable oil obtained from seeds flowers, fruits, leaves, stem, or any part of a plant or a tree including cotton seed oil, soy bean oil, almond oil, sunflower oil, peanut oil, sesame oil.

↓

SOLUTION OF POLYMER + PLASTICIZER IN VOLATILE SOLVENT(S)

↓

HEAT AND/OR APPLY VACUUM TO EVAPORATE THE VOLATILE SOLVENT

↓

BIODEGRADABLE FREE-FLOWING LIQUID, VISCOUS LIQUID, GEL OR PASTE (BLANK FORMULATION)
+
BIOLOGICALLY ACTIVE SUBSTANCE(S) OR BAS

↓

BAS-LOADED BIODEGRADABLE DELIVERY SYSTEM

(FREE-FLOWING LIQUID OR SUSPENSION WITH DISSOLVED OR SUSPENDED BAS RESPECTIVELY, VISCOUS LIQUID OR SUSPENSION WITH DISSOLVED OR SUSPENDED BAS RESPECTIVELY, OR GEL WITH DISSOLVED OR SUSPENDED BAS, OR PASTE WITH DISSOLVED OR SUSPENDED BAS)

FIGURE 2

| BIODEGRADABLE POLYMERS | VOLATILE SOLVENTS |
|---|---|
| Polylactic acid (PLA) | Acetone |
| Polylactic-co-glycolic acid (PLGLY) | Ethyl acetate |
| Polyaminoacids | Chloroform |
| Polyhydroxybutyric and | Methyl acetate |
| Valeric acid copolymers (PHBV) | Methylene chloride |
| Poly-ε-caprolatone (PCL) | Methylethyl ketone |
| Lactic acid and caprolactone copolymer | |

↓

SOLUTION OF POLYMER IN VOLATILE SOLVENT(S)
+
PLASTICIZER

Triethyl citrate (TEC), Acetyl triethyl citrate (ATEC), Tributyl citrate (TBC), Acetyl tributyl citrate (ATBC), Glyceryl triacetate (Triacetin), Dimethyl phthalate (DMP), Diethyl phthalate (DEP), dioctyl phthalate, 2-pyrrolidone (2-Pyrrol®), Diethylene glycol monoethyl ether (Transcutol®), n-methyl pyrrolidone (NMP), polyethylene glycols (PEG), PEG-8 glyceryl caprylate/caprate (Labrasol®), propylene carbonate, gamma butyrolactone, dipropylene glycol methyl ether acetate (DPM acetate), vegetable oil obtained from seeds, flowers, fruits, leaves, stem, or any part of a plant or a tree including cotton seed oil, soy bean oil, almond oil, sunflower oil, peanut oil, sesame oil.

↓

SOLUTION OF POLYMER + PLASTICIZER IN VOLATILE SOLVENT(S)
+
BIOLOGICALLY ACTIVE SUBSTANCE(S) OR BAS

↓

HEAT AND/OR APPLY VACUUM TO EVAPORATE THE VOLATILE SOLVENT

↓

BAS-LOADED BIODEGRADABLE DELIVERY SYSTEM

(FREE-FLOWING LIQUID OR SUSPENSION WITH DISSOLVED OR SUSPENDED BAS RESPECTIVELY, VISCOUS LIQUID OR SUSPENSION WITH DISSOLVED OR SUSPENDED BAS RESPECTIVELY, OR GEL WITH DISSOLVED OR SUSPENDED BAS, OR PASTE WITH DISSOLVED OR SUSPENDED BAS)

Effect of Varying Solubility of Drug on Oxytetracycline Released from Biodegradable Gels

BIODEGRADABLE DELIVERY SYSTEMS OF BIOLOGICALLY ACTIVE SUBSTANCES

This application is related to U.S. Provisional Application No. 60063680 filed Oct. 29, 1997.

FIELD OF THE INVENTION

The present invention relates to biodegradable delivery systems incorporating a biologically active substance (BAS). The present invention also provides methods for preparing these biodegradable delivery systems. The consistency and rheology, in vivo degradation rates of the biodegradable delivery systems, and release characteristics of the BAS from the biodegradable delivery system is controlled by modulating the type and concentration of plasticizers, and type and molecular weight of polymers and copolymers.

BACKGROUND OF THE INVENTION

The term biodegradable polymers refers to those polymers which are slowly converted to nontoxic degradation products in the body. Examples of biodegradable polymers include polylactic acid, polyglycolic acid, polycaprolactone, polyhydroxybutyrate, polyhydroxyvalerate, poly(alkylcyanoacrylate), polyanhydrides, polyorthoesters, poly(aminoacids), pseudopolyamino acids, polyphosphazenes. Some of these polymers and their copolymers have been studied extensively for biomedical applications such as sutures, staples and mesh for wound closure, fracture fixation, bone augmentation and ligament reconstruction in orthopedics, ligation clips and vascular grafts in cardiovascular surgery, and dental repairs (Barrows T. Degradable implant materials: a review of synthetic absorbable polymers and their applications. Clinical materials., 1:233–257, 1986). They have also been used to prepare biodegradable drug delivery systems capable of releasing the drug or a biologically active substance over the desired length of time.

The advantages of using biodegradable polymers in biodegradable delivery systems of BAS are: ready availability of polymers, polymers used are nontoxic, biocompatibile and biodegradable, facile predictability of biodegradation rates of the polymers, ease of modification of the degradation characteristics of the polymers, regulatory approval of some of the commonly used biodegradable polymers, ease of fabrication of the polymers into various types of devices and the possibility of controlling the release of BAS by polymers over the desired length of time.

Release of a BAS from a polymeric delivery system depends on the physicochemical characteristics of the BAS molecule, polymer and other excipients, and the dosage form. The important factors governing BAS release characteristics from the delivery systems prepared with biodegradable polymers are polymer molecular weight, copolymer ratio, polymer hydrophilicity or lipophilicity, degree of plasticization, particle size and percentage of BAS-loading, hydrophilicity or lipophilicity of the incorporated BAS, solubility of the BAS in both the delivery system and in the biological fluids, physical form of the formulation (i.e. solution, suspension, gel or paste), and the method of preparation of the delivery system.

Several types of BAS delivery systems have been prepared from biodegradable polymers. These include microparticles such as microspheres and microcapsules (Schindler A, Jeffcoat R, Kimmel G L, Pitt C G, Wall M E and Zwelinger R., in: Contemporary Topics in Polymer Science, Pearce E M and Schaefgen J R, eds., Vol. 2, Plenum Publishing Corporation, New York, pp. 251–289, 1977; Mason N S, Gupta D V S, Keller, D W, Youngquist R S, and Sparks R F. Biomedical applications of microencapsulation, (Lim F, ed.), CRC Press Inc., Florida, pp. 75–84, 1984; Harrigan S E, McCarthy D A, Reuning R and Thies C., Midl. Macromol. Monograph, 5:91–100, 1978. ; Sanders L M, Burns R, Bitale K and Hoffman P., Clinical performance of nafarelin controlled release injectable: influence of formulation parameters on release kinetics and duration of efficacy., Proceedings of the International Symposium on Controlled Release and Bioactive Materials, 15:62–63, 1988; Mathiowitz E, Leong K and Langer R., Macromolecular drug release from bioerodible polyanhydride microspheres, in: Proceedings of the 12th International Symposium on Controlled Release of Bioactive Materials, Peppas N and Haluska R, eds., pp. 183, 1985), films (Jackanicz T M, Nash H A, Wise D L and Gregory J B. Polylactic acid as a biodegradable carrier for contraceptive steroids., Contraception, 8:227–233, 1973. ; Woodland J H R, Yolles S, Blake A B, Helrich M and Meyer F J. Long-acting delivery systems for narcotic antagonist. I. J. Med. Chem., 16:897–901, 1973), fibers (Eenink M J D, Maassen G C T, Sam A P, Geelen J A A, van Lieshout J B J M, Olijslager J, de Nijs H, and de Jager E. Development of a new long-acting contraceptive subdermal implant releasing 3-ketodesogeatrel., Proceedings of the 15th International Symposium on Controlled Release of Bioactive Materials, Controlled Release Society, Lincolnshire, Ill., pp.402–403, 1988), capsules (Sidman K R, Schwope A D, Steber W D, Rudolph S E, Paulin S B. Biodegradable, implantable sustained release systems based on glutamic acid copolymers. J. Membr. Sci., 7:277–291, 1980; Pitt C G, Gratzl M M, Jeffcoat M A, Zweidinger R and Schindler A. Sustained drug delivery systems II: Factors affecting release rates from poly-$\epsilon$-caprolactone and related biodegradable polyesters., J. Pharm. Sci., 68(12):1534–1538, 1979), discs (Cowsar D R, Dunn R L., Biodegradable and non-biodegradable fibrous delivery systems, in: Long acting Contraceptive Delivery Systems, Zatuchni G I, Goldsmith A, Shelton J D and Sciarra J J, eds., Harper & Row, Publishers, Philadelphia, pp.145–148, 1984), wafers (Brem et al., J. Neurosurgery, 74:441–446, 1991), and solutions (Dunn et al., U.S. Pat. Nos. 4,938,763; 5,324,519; 5,324,520; 5,278,201; 5,340,849; 5,368,859; 5,660849; 5,632,727; 5,599,552; 5,487,897). All of these, with the exception of microparticles and solutions, need to be surgically implanted. This procedure is inconvenient and undesirable. Drug-loaded microspheres and solutions, on the other hand, can be easily injected. However, there are several inherent disadvantages of microparticles. These include the need for reconstitution before injection, the inability to remove the dose once it is injected, and the relative complicated manufacturing procedure.

While solutions described in patents by Dunn et al. offer the distinct advantage of ease of injection, an inherent disadvantage to the method of preparing solutions, as indicated in the patents is that, the amount of polymer which can be incorporated into n-methylpyrrolidone (NMP), the solvent of choice cited in their inventions, appears to be limited. This is particularly true when higher concentrations of high molecular weight polymers have to be dissolved in NMP by the method cited in the patents by Dunn et al. Therefore, there clearly exists a need for developing easily injectable, implantable or applicable biodegradable BAS delivery systems such as free-flowing and viscous liquids, gels, and pastes prepared from biodegradable polymers using alternative methods.

SUMMARY OF THE PRESENT INVENTION

The present invention relates to methods for preparing biodegradable delivery systems with or without biologically active substances (BAS). These biodegradable delivery systems are comprised of biodegradable polymers and plasticizers. The present invention also relates to the use of BAS-loaded delivery systems for obtaining controlled release delivery system of a BAS over a desired length of time. The resulting formulations may be either free-flowing or viscous liquids where the BAS is completely dissolved in the polymer-plasticizer blended liquids, or free-flowing or viscous suspensions where the BAS is suspended in the free-flowing or viscous polymer-plasticizer blended liquids. They can also be gels with dissolved or suspended BAS, or pastes with dissolved or suspended BAS.

The method of the present invention involves dissolving one or more biodegradable polymers and one or more plasticizers in a volatile solvent or mixture of volatile solvents. The BAS may then be added to this mixture. The volatile solvent is then removed using vacuum or evaporated at an elevated temperature, or removed using both vacuum and elevated temperature. The resulting BAS-loaded formulation provides controlled release of the biologically active substance over the desired length of time. Alternatively, a blank formulation may be first prepared by the aforementioned method without incorporating the BAS in the formulation. Appropriate quantities of one or more BAS are then added to this formulation to form a BAS-loaded formulation which controls the release of the BAS over the desired length of time.

Advantages of biodegradable delivery systems of the present invention include ease of manufacturing, injection, implantation and application, ease of incorporation of BAS into the delivery system, facile tailoring of the release of BAS from the biodegradable delivery system, ease of control over the consistency or rheology of the biodegradable delivery system, and control of in vivo biodegradation rates of delivery system.

The blank formulation without a BAS may be used as a biodegradable tissue or cavity filler or spacer in the body, whereas, BAS-loaded biodegradable delivery system may be used for the treatment of a variety of diseases and pathological conditions. The composition of the invention may be injected, implanted or applied in animals and humans.

Alternatively, if the blank formulation is loaded with antigen or antigens, the resulting biodegradable delivery system may be used to generate specific antibodies following injection, implatation or application in animals or humans.

BRIEF DESCRIPTION OF THE DRAWINGS

FIG. 1 shows a method of preparing a biodegradable delivery system.

FIG. 2 shows an alternate method of preparing a biodegradable delivery system.

DETAILED DESCRIPTION OF THE INVENTION

Figure 3:
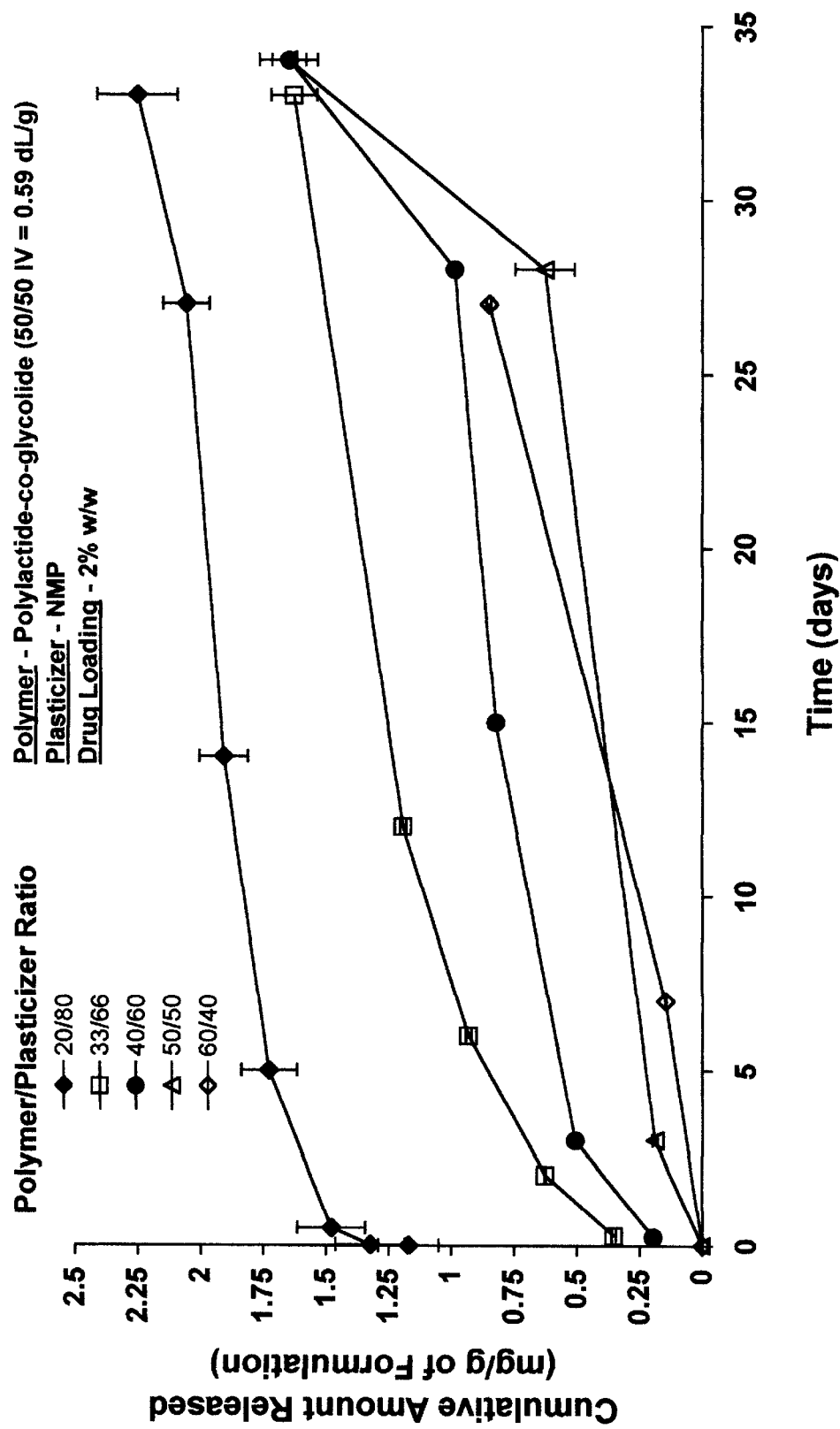
FIG. 3 describes the effect of varying polymer-to-plasticizer ratio on cumulative amount of levonorgestrel released.

The present invention relates to the composition of biodegradable delivery systems. These delivery systems comprise of at least one polymer and at least one plasticizer. The delivery system of the present invention may also comprise of at least one biologically active substance (BAS).

According to the present invention, the term polymer includes oligomer, copolymer and terpolymer. Biodegradable polymers are used in this invention because they form matrices that can control the release of BAS over a desired length of time, can degrade in vivo into non-toxic degradation products, and are available in varying physicochemical properties including varying hydrophilicity and hydrophobicity, varying crystallinity and amorphous states, and varying solubility in solvents. Moreover, tailoring the release charactertics of the BAS from the biodegradable delivery systems, varying the consistency or rheology of the matrix formulation, and fabrication of the system with and without BAS can be easily achieved using this invention.

In the present invention, plasticizers are used in varying ratios to convert a polymer from a solid state to a polymer-matrix of varying consistency such as a free-flowing or a viscous liquid, a gel or a paste. Plasticizers are chemicals added to polymers to improve their flow, and therefore their processibility (Billmeyer, F., Jr. Textbook of Polymer Science, John Wiley and Sons, New York, 1984, p. 472). This is achieved by lowering their glass transition temperature (a temperature at which a glassy polymer becomes rubbery on heating and a rubbery polymer reverts to a glassy one on cooling), thus achieving a change in properties. A plasticizer can only plasticize a polymer when the molecules of the plasticizer can interact with the molecules of the polymer. Hence, the plasticizers act as lubricants between the polymer chains, facilitating slippage of chain past chain under stress and extending the temperature range for segmental rotation to lower temperatures (Martin, A., Physical Pharmacy, Lea and Febiger, Philadelphia, 1993, p. 588). The degree or extent of plasticization of a polymer will depend on the amount of plasticizer blended with the polymer. Higher the concentration of the plasticizer, greater the extent of plasticization or flexibility of the polymer. If a plasticizer and a polymer are fully compatible with each other, then depending on the concentration of the plasticizer blended with the polymer, it is possible to obtain a polymer matrix of varying consistency or rheology such as a free-flowing or viscous liquid, gel or paste. Moreover, since plasticizers are available with varying physicochemical properties, including varying hydrophilicity and lipophilicity, it is possible to blend an appropriate plasticizer at a desired concentration with a selected compatible polymer such that the resulting polymer matrix has the tailored physicochemical characteristics, including varying hydrophilicity and lipophilicity, and consistency. The present invention also includes formulations wherein two or more plasticizers are used in a combination or blend of varying ratios.

The present invention relates to the use of BAS-loaded delivery systems for obtaining controlled release of the BAS over the desired length of time. The resulting delivery systems may be free-flowing or viscous liquids or gels or pastes wherein the BAS is completely dissolved in the polymer-plasticizer blended liquids. The delivery systems could also be free-flowing or viscous suspensions wherein the BAS is suspended in the free-flowing or viscous polymer-plasticizer blended liquids, or gels with dissolved or suspended BAS, or pastes with dissolved or suspended BAS. The consistency or rheology, physicochemical properties, physical form of the biodegradable delivery system (i.e. a solution in which the BAS is completely dissolved or a suspension where the BAS is suspended in the delivery system), rate and duration of in vivo biodegradation, and BAS release characteristics depend on a number of factors. These include: physicochemical properties of polymers such as type, molecular weight, glass-transition temperature, hydrophilicity and lipophilicity, concentration of the polymer; physicochemical properties of plasticizer such as type, hydrophilicity and lipophilicity, boiling point or melting point; and physicochemical properties of BAS such as type, hydrophilicity and lipophilicity, molecular weight, melting point or boiling point. In addition, the physicochemical interactions between the polymer, plasticizer and BAS also affect the rate and duration of in vivo biodegradation, and BAS release characteristics. For example, using the present invention, it is possible to tailor the release of a BAS (with specific physicochemical properties and the desired in vivo concentration), for the desired length time. This is achieved by blending an appropriately selected polymer with an appropriately selected plasticizer or mixtures of plasticizers. Besides controlling the release charactertistics of the BAS from the delivery system described in the present invention, an appropriate blend of the polymer and plasticizer also controls the consistency and rheology of the delivery system. It is also possible to extend the in vivo duration of stay of the delivery system by selecting a higher molecular weight polymer, since polymers with higher molecular weights generally degrade slowly in the body.

Methods of preparing the biodegradable delivery system of the present invention involve dissolving at least one biodegradable polymer in a volatile solvent or a mixture of solvents.

Polymers suitable for preparing the biodegradable delivery systems of the present invention include, but are not limited to, polyesters, polyorthoesters, polyanhydrides, polyaminoacids, pseudopolyamino acids, polyamides, polyalkylcyanoacrylates, and polyphosphazenes. In a preferred embodiment, polymers include polylactic acid and its copolymers, polyglycolic acid and its copolymers, polycaprolactone and its copolymers, polyhydroxybutyrates and their copolymers, and polyhydroxyvalerates and their copolymers. A mixture of polymers may be used to tailor either the release characteristics of BAS in the biodegradable delivery system, or the degradation characteristics of the biodegradable delivery system or both.

Solvents used to dissolve the polymer for the preparation of biodegradable delivery system of the present invention include, but are not limited to, ketones, ethers, alcohols, amides, and chlorinated solvents. Preferred solvents are acetone, ethyl acetate, methyl acetate, methylethylketone, chloroform, methylene chloride, isopropanol, ethyl alcohol, ethyl ether, methylethyl ether, hexafluroisopropanol, tertrahydrofuran, and hexafluroacetone sesquihydrate . A mixture of volatile solvents may also be used to create a suitable mixture which can dissolve both the polymer and the plasticizer.

Plasticizers used for the preparation of biodegradable delivery system of the present invention include, but are not limited to, citrates such as diethyl citrate (DEC), triethyl citrate (TEC), acetyl triethyl citrate (ATEC), tributyl citrate (TBC), acetyl tributyl citrate (ATBC), phthalates such as dimethyl phthalate (DMP), diethyl phthalate (DEP), triethyl phthalate (TEP), dibutyl phthalate (DBP), dioctyl phthalate, glycol ethers such as ethylene glycol diethyl ether, propylene glycol monomethyl ether, ethylene glycol monoethyl ether, diethylene glycol monoethyl ether (Transcutol®), propylene glycol monotertiary butyl ether, dipropylene glycol monomethyl ether, 2 pyrrolidone (2-Pyrrol®), propylene glycol, glycerol, sorbitol, butyryltri-n-hexyl-citrate, acetyltri-n-hexyl citrate, sebacates such as dibutyl sebacate, tributyl sebacate, dipropylene glycol methyl ether acetate (DPM acetate), propylene carbonate, propylene glycol laurate, propylene glycol caprylate/caprate, gamma butyrolactone, polyethylene glycols (PEG), vegetable oils obtained from seeds, flowers, fruits, leaves, stem or any part of a plant or tree including cotton seed oil, soy bean oil, almond oil, sunflower oil, peanut oil, sesame oil, glycerol and PEG esters of acids and fatty acids (Gelucires®, Labrafils® and Labrasol®) such as PEG-6 glycerol mono oleate, PEG-6 glycerol linoleate, PEG-8 glycerol linoleate, PEG-4 glyceryl caprylate/caprate, PEG-8 glyceryl caprylate/caprate, polyglyceryl-3-oleate, polyglyceryl-6-dioleate, polyglyceryl-3-isostearate, PEG-32 glyceryl laurate (Gelucire 44/1®), PEG-32 glyceryl palmitostearate (Gelucire 50/13®), PEG-32 glyceryl stearate (Gelucire 53/10®), glyceryl behenate, cetyl palmitate, glyceryl di and tri stearate, glyceryl palmitostearate, and glyceryl triacetate (Triacetin®). The use of two or more plasticizers in a combination or blend of varying ratios is also encompassed by the present invention.

BAS may be added to the solution of polymer and plasticizer in a volatile solvent. Alternatively, the BAS may be added to the blank formulation (which has been formulated with at least one polymer and one plasticizer, without the BAS) prior to in vivo injection, implantation or application in an animal or human.

Examples of BAS include, but are not limited to, steroids, hormones, antipsychotic agents, agents that act on the central nervous system (CNS—agents), fertility regulating agents, antibodies and antigens, anesthetics, analgesics, antibiotics, antiviral agents, antineoplastic agents, antifungal agents, cavity and infection preventing agents, cardiovascular agents, antiinflammatory agents, vasodilators, brochiodilators, alkaloids, peptides and proteins, agents or extracts derived from whole or parts of plants, trees, flowers, fruits, buds, leaves, barks, stem, roots, and animal tissues, growth promoting agents, soft and hard tissue growth promoting agents, natural tissues such as bones or agents derived therefrom, bone growth promoting agents such as calcium phosphates and hydroxyapatites, whole viable cells and cell-lines, and biological tissues such as islets of langerhans and pancreas.

The biodegradable delivery systems of the present invention are prepared by dissolving at least one biodegradable polymer in a volatile solvent. Following this, at least one plasticizer is added to the polymer solution. This solvent is evaporated using vacuum or removed at an elevated temperature, or evaporated using a combination of both vacuum and elevated temperature, resulting in the formation of biodegradable delivery system in the form of either free-flowing or viscous liquids, gels or pastes. This formulation is referred to as a blank formulation. A BAS may next be added to the blank formulation to obtain a delivery system in the form of free-flowing or viscous liquid where the BAS is completely dissolved in the polymer-plasticizer blended liquids, or free-flowing or viscous suspensions where the BAS is suspended in the free-flowing or viscous polymer-plasticizer blended liquids, or gels with dissolved or suspended BAS, or pastes with dissolved or suspended BAS. This system provides controlled release of the BAS over the desired length of time. The procedure for preparing a blank formulation first, followed by a BAS-loaded delivery system is shown in FIG. 1.

Alternatively, the BAS may be added to the polymer and plasticizer solution in a volatile solvent. The volatile solvent is then removed in vacuum or at an elevated temperature or using a combination of both vacuum and elevated temperature. This procedure is shown in FIG. 2.

The blank formulation without a BAS may be used as a biodegradable tissue or cavity filler or spacer in the body, whereas, BAS-loaded biodegradable delivery system may be used for the treatment of a variety of diseases and pathological conditions. The composition of the invention may be injected, implanted or applied in animals and humans. For example, the biodegradable delivery system loaded with an antitumor agent can be directly injected into a solid tumor or implanted in the brain, thus affording site-specific delivery for disease states that are otherwise very difficult, if not impossible to treat using the conventional methods of treatment. The system could be loaded with a contraceptive agent, antipsychotic agent, anticonvulsants, antimalarial, antihypertensive agent, antibiotics, antiviral agents, and biologically active protein and peptides, and injected subcutaneously or intramuscularly to provide a controlled release of the agents for the desired length of time. Drugs such as antiinflammatory agents, analgesics and anesthetics could be injected directly into joints or sites in the body from where the pain is emanating, thus providing relief from the excruciating pain and making the joints more mobile. Antigens may also be incorporated into the delivery system and injected, implanted or applied in animals or humans to induce the production of specific antibodies.

This invention will be understood with greater particularity by reviewing the following examples:

EXAMPLES

Example 1

Preparation of a Blank Formulation of a Biodegradable Delivery System:

A polymer (50% w/w of 50/50 lactide-co-glycolide copolymer) was dissolved in minimum quantity of acetone. Triethyl citrate (TEC), at a concentration of 50% w/w, was added to the polymer solution and was stirred to yield a uniform mixture. Acetone was evaporated from the mixture by heating at 60–75° C. with constant stirring. The resulting formulation obtained was a matrix with a gel-like consistency.

Example 2

Example 1 was repeated using 10% w/w of 50/50 lactide-co-glycolide copolymer and 90% w/w TEC. The resulting formulation obtained was a matrix with a liquid-like consistency.

Example 3

Example 1 was repeated using 20% w/w of 50/50 lactide-co-glycolide copolymer and 80% w/w TEC. The resulting formulation obtained was a matrix with a viscous liquid-like consistency.

Example 4

Example 1 was repeated, using 30% w/w of 50/50 lactide-co-glycolide copolymer and 70% w/w TEC was used. The resulting formulation obtained was a matrix with a viscous liquid-like consistency.

Example 5

Example 1 was repeated, using 40% w/w of 50/50 lactide-co-glycolide copolymer and 60% w/w TEC was used. The resulting formulation obtained was a matrix with a viscous liquid-like consistency.

Example 6

Example 1 was repeated, using 60% w/w of 50/50 lactide-co-glycolide copolymer and 40% w/w TEC was used. The resulting formulation obtained was a matrix with a gel-like consistency.

Example 7

Example 1 was repeated, using 70% w/w of 50/50 lactide-co-glycolide copolymer and 30% w/w TEC was used. The resulting formulation obtained was a matrix with a gel-like consistency.

Example 8

Example 1 was repeated, using 80% w/w of 50/50 lactide-co-glycolide copolymer and 20% w/w TEC was used. The resulting formulation obtained was a matrix with thick sticky paste.

Example 9

Example 1 was repeated with the following polymers and plasticizers as shown in Table 1 below:

TABLE 1

| TYPE OF POLYMER | PLASTICIZER | SOLVENT | DESCRIPTION OF THE FORMULATION |
|---|---|---|---|
| DL-POLYLACTIC ACID (DL-PLA; I.V. = 0.58) | GLYCERYL TRIACETATE (TRIACETIN) | ACETONE | GEL, SLIGHTLY CLOUDY |
| DL-POLYLACTIC ACID (DL-PLA; I.V. = 0.58) | TRIETHYL CITRATE (TEC) | ACETONE | GEL, TRANSPARENT |
| DL-POLYLACTIC ACID (DL-PLA; I.V. = 0.58) | ACETYL TRIETHYL CITRATE (ATEC) | ACETONE | GEL, SLIGHTLY CLOUDY |
| DL-POLYLACTIC ACID (DL-PLA; I.V. = 0.58) | DIMETHYL PHTHALATE (DMP) | ACETONE | GEL, LESS VISCOUS, TRANSPARENT |
| DL-POLYLACTIC ACID (DL-PLA; I.V. = 0.58) | DIETHYL PHTHALATE (DEP) | ACETONE | GEL, TRANSPARENT |
| DL-POLYLACTIC-CO-GLYCOLIC ACID (DL-PLGLA; I.V. = 0.58) | GLYCERYL TRIACETATE (TRIACETIN) | ACETONE | GEL, LESS VISCOUS, SLIGHTLY YELLOW |
| DL-POLYLACTIC-CO-GLYCOLIC ACID (DL-PLGLA; I.V. = 0.58) | TRIETHYL CITRATE (TEC) | ACETONE | GEL, SLIGHTLY YELLOW |
| DL-POLYLACTIC-CO-GLYCOLIC ACID (DL-PLGLA; I.V. = 0.58) | ACETYL TRIETHYL CITRATE (ATEC) | ACETONE | GEL, SLIGHTLY YELLOW |
| DL-POLYLACTIC-CO-GLYCOLIC ACID (DL-PLGLA; I.V. = 0.58) | TRIETHYL CITRATE (TEC) | ACETONE | GEL, SLIGHTLY YELLOW |
| DL-POLYLACTIC-CO-GLYCOLIC ACID (DL-PLGLA; I.V. = 0.58) | DIMETHYL PHTAALATE (DMP) | ACETONE | GEL, LESS VISCOUS, TRANSPARENT |
| DL-POLYLACTIC-CO-GLYCOLIC ACID (DL-PLGLA; I.V. = 0.58) | DIETHYL PHTHALATE (DEP) | ACETONE | GEL, SLIGHTLY YELLOW |
| DL-POLYLACTIC-CO-GLYCOLIC ACID (DL-PLGLA; I.V. = 0.58) | N-METHYL PYRROLIDONE (NMP) | ACETONE | VISCOUS LIQUID, TRANSPARENT |
| DL-POLYLACTIC-CO-GLYCOLIC ACID (DL-PLGLA; I.V. = 0.15) | GLYCERYL TRIACETATE (TRIACETIN) | ACETONE | VISCOUS LIQUID, TRANSPARENT |
| DL-POLYLACTIC-CO-GLYCOLIC ACID (DL-PLGLA; I.V. = 0.15) | TRIETHYL CITRATE (TEC) | ACETONE | VISCOUS LIQUID, TRANSPARENT |
| DL-POLYLACTIC-CO-GLYCOLIC ACID (DL-PLGLA; I.V. = 0.15) | ACETYL TRIETHYL CITRATE (ATEC) | ACETONE | VISCOUS LIQUID, TRANSPARENT |
| DL-POLYLACTIC-CO-GLYCOLIC ACID (DL-PLGLA; I.V. = 0.15) | TRIETHYL CITRATE (TEC) | ACETONE | VISCOUS LIQUID, TRANSPARENT |

Example 10

Several polymer were separately dissolved in several volatile solvents. Several plasticizer were separately added to the polymer-solution, such that the ratio of polymer to plasticizer if the final formulation ranged from 1:19 to 4:1. Several drugs were separately added to the polymer-plasticizer-solvent blends. The solvents were then evaporated at an elevated temperature to obtain drug-loaded formulation. The drug content in the final formulations constituted up to 50% w/w.

For several formulation, blank formulation of polymers and plasticizers blends were first obtained. The drugs were then separately added to the blank formulations to obtain drug-loaded formulations. Table 2 lists examples of polymers, plasticizers, solvents, polymer to plasticizer ratio and concentration of drugs in the formulations.

TABLE 2

| TYPE OF POLYMERS | PLASTICIZERS | SOLVENTS | POLYMER TO PLASTICIZER RATIOS | DRUGS | CONCENTRATION OF DRUGS (% w/w) IN POLYMER MATRICES |
|---|---|---|---|---|---|
| POLYCAPROLACTONE | DIETHYLENE GLYCOL | METHYLENE CHLORIDE | 1:1 | TESTOSTERONE | |
| | | | 1:2 | PROGESTERONE | 0.5%–50% w/w |
| POLYLACTIC ACID | MONOETHYL ETHER (TRANSCUTOL ®), | CHLOROFORM ACETONE | 1:3 | LEVONORGESTRUEL | |
| | | | 1:4 | THEOPHYLLINE | |
| POLYLACTIC-CO-GLYCOLIC ACID | PEG-8-GLYCERYL CAPRYLATE/ | ETHYL ACETATE | 1:9 | PROPRANOLOL | |
| | | | 1:19 | ATENOLOL | |
| COPOLYMERS OF LACTIC ACID AND | CAPRATE (LABRASOL ®) | | 2:1 | METROPROLOL | |
| | | | 2:3 | CHLORPROAMAZINE | |
| CAPROLACTONE | TRIETHYL CITRATE (TEC), ACETYL TRIETHYL CITRATE (ATEC) GLYCERYL TRIACETATE (TRIACETIN ®) POLYETHYLENE GLYCOLS (PEG) N-METHYL PYRROLIDONE (NMP) | | 3:2 | CLONIDINE | |
| | | | 3:1 | THEOPHYLLINE | |
| | | | 4:1 | INSULIN | |
| | | | | OXYTETRACYCLINE | |
| | | | | NALTREXONE | |

Example 11

Effect of Varying Polymer-to-plasticizer Ratios on the Physical State of Formulations and Drug Release Characteristics Several samples of polylactic-co-glycolic acid (inherent viscosoty-0.59) were weighed and separately dissolved in acetone. Varying ratios of N-methyl pyrrolidone (NMP) were separately added to the polymer-solutions, such that the ratio of polymer to plasticizer in the formulations ranged from 20:80 to 80:20. Acetone was then evaporated by heating the solutions at 70–80° C. Levonorgestrel (2% w/w) was added to the resulting formulations. Table 3 describes the physical state of the formulations containing varying polymer-to-plasticizer ratios. Drug release cahracteristics from the formulations depicted in Table 3 are shown in FIG. 3.

TABLE 3

Physical state of formulations containing varying polymer-to-plasticizer ratios

| Polymer*-to-NMP Ratio | Physical State of the Formulation | Physical State of Drug in the Formulation |
| --- | --- | --- |
| 20:80 | Very flowable liquid | Dissolved |
| 40:60 | Viscous liquid | Dissolved initially; however precipitated partially after 48 hrs |
| 50:50 | Flowable gel | Suspended |
| 60:40 | Flowable gel | Suspended |
| 80:20 | Thick paste | Suspended |

*50/50 Polylactide-co-glycolide (IV = 0.59 dL/g)
Drug loading = 2% w/w

Example 12

Figure 4:
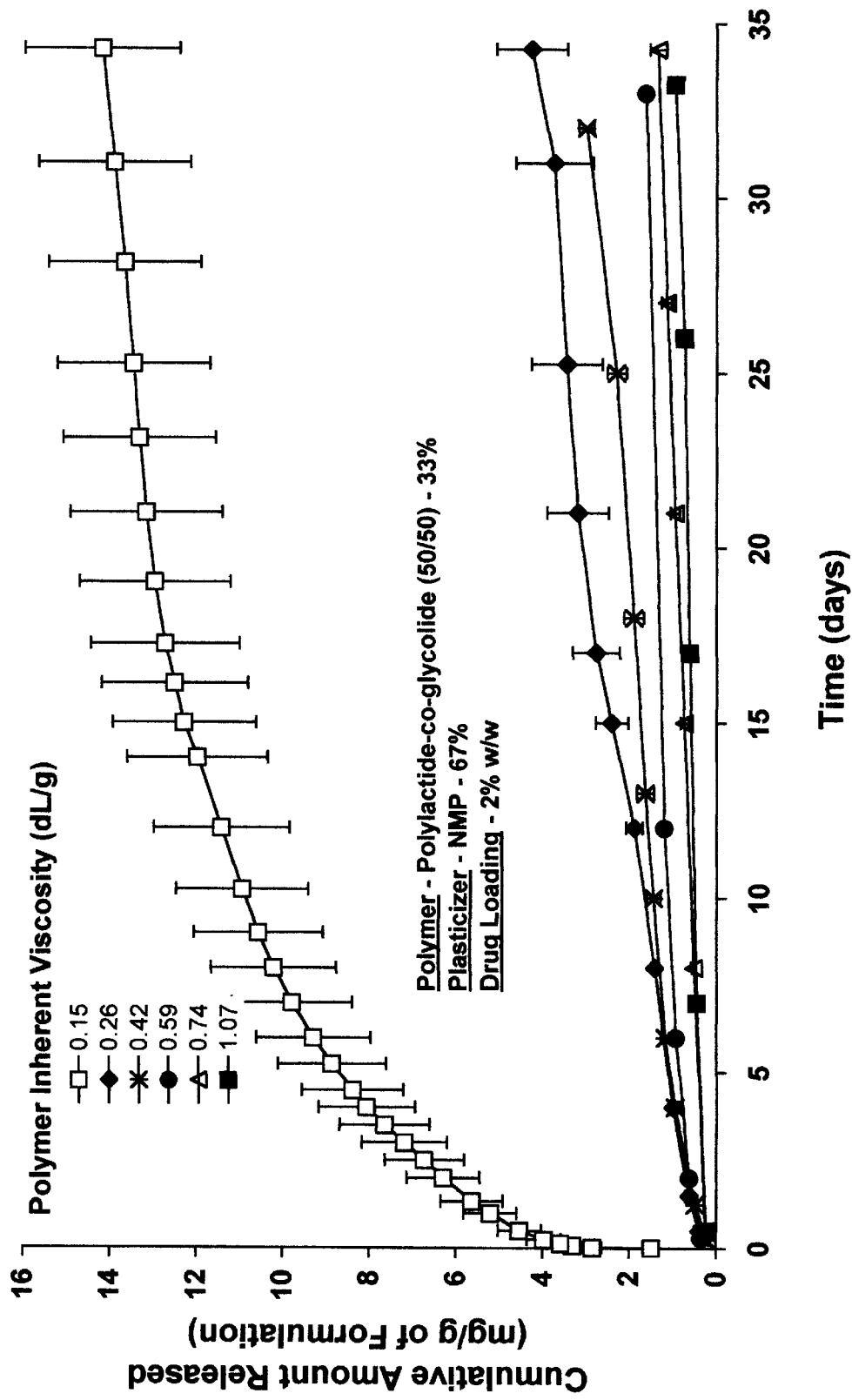
FIG. 4 describes the effect of varying polymer inherent viscosity on cumulative amount of levonorgestrel released.

Effect of Varying Polymer Inherent Viscosities on the Physical State of the Formulations and Drug Release Characteristics Several samples of polylactic-co-glycolic acid (PLGLA) with varying inherent viscosities ranging from 0.15–1.07 were weighed and separately dissolved in acetone. An appropriate quantity of N-methyl pyrrolidone (NMP) was added to the polymer-solutions such that the ratio of polymer to plasticizer in the formulations was 33% PLGLA and 67% NMP. Acetone was then evaporated by heating the solutions at 70–80° C. Levonorgestrel (2% w/w) was added to the resulting formulations. Table 4 describes the physical state of the formulations containing varying polymer inherent viscosities. Drug release characteristics from the formulations depicted in Table 4 are shown in FIG. 4.

TABLE 4

Physical state of formulations containing varying polymer inherent viscosities

| Polymer Inherent Viscosity (dL/g) | Physical State of the Formulation* | Physical State of Drug in the Formulation* |
| --- | --- | --- |
| 0.15 | Very flowable liquid | Dissolved |
| 0.26 | Flowable liquid | Dissolved |
| 0.42 | Flowable liquid | Dissolved |
| 0.59 | Viscous liquid | Dissolved |
| 0.74 | Flowable gel | Dissolved |
| 1.07 | Viscous gel | Dissolved |

33% w/w of 50/50 Polylactide-co-glycolide and 67% w/w NMP
Drug loading = 2% w/w

Example 13

Figure 5:
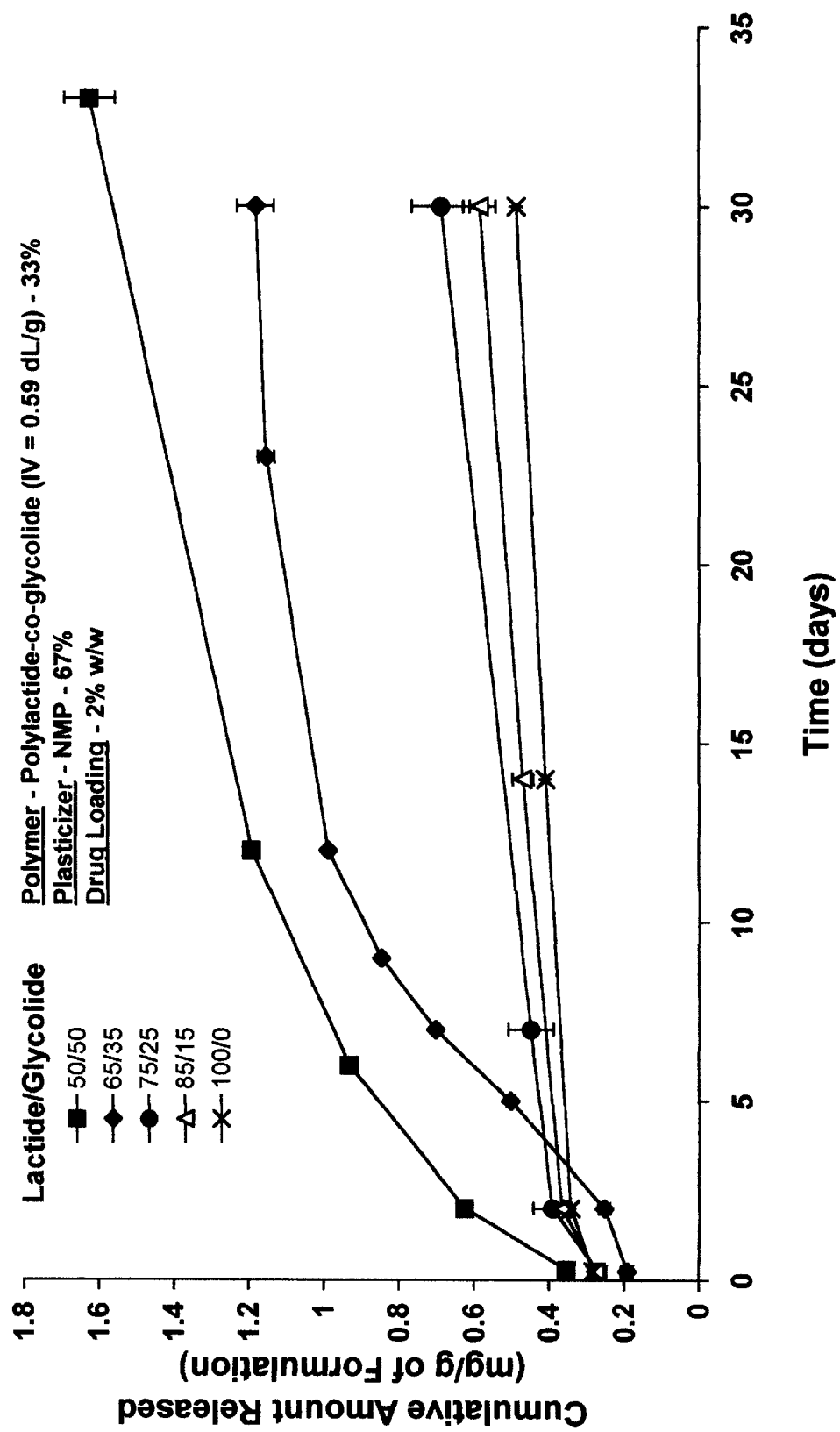
FIG. 5 describes the effect of varying copolymer ratio on cumulative amount of levonorgestrel released.

Effect of Varying Polymer Inherent Viscosities on Physical State of Formulations and Drug Release Characteristics Samples of pure polylactic acid and polylactic-co-glycolic acid (PLGLA) with varying copolymer ratios ranging from 50/50 to 85/15 were weighed and separately dissolved in acetone. An appropriate quantity of N-methyl pyrrolidone (NMP) was added to the polymer-solutions such that the ratio of polymer to plasticizer in the formulations was 33% PLGLA and 67% NMP. Acetone was then evaporated by heating the solutions at 70–80° C. Levonorgestrel (2% w/w) was added to the resulting formulations. Table 5 describes the physical state of the formulations prepared from varying copolymer ratios. Drug release characteristics from the formulations depicted in Table 5 are shown in FIG. 5.

TABLE 5

Physical state of formulations containing varying copolymer ratios.

| Ratio of Lactide to Glycolide in Polymer | Physical State of the Formulation* | Physical State of Drug in the Formulation* |
| --- | --- | --- |
| 50/50 | Yellowish, viscous liquid | Dissolved |
| 65/35 | Yellowish, viscous liquid | Dissolved |
| 75/25 | Pale yellow, highly viscous liquid | Dissolved |
| 85/15 | Straw colored, slightly translucent, highly viscous liquid | Dissolved |
| 100/0 | Clear, highly viscous liquid | Dissolved |

*33% w/w of 50/50 Polylactide-co-glycolide (IV = 0.59 dL/g) and 67% w/w NMP
Drug loading = 2% w/w

Example 14

Effect of Varying Drug Loadings on Drug Release

Figure 6:
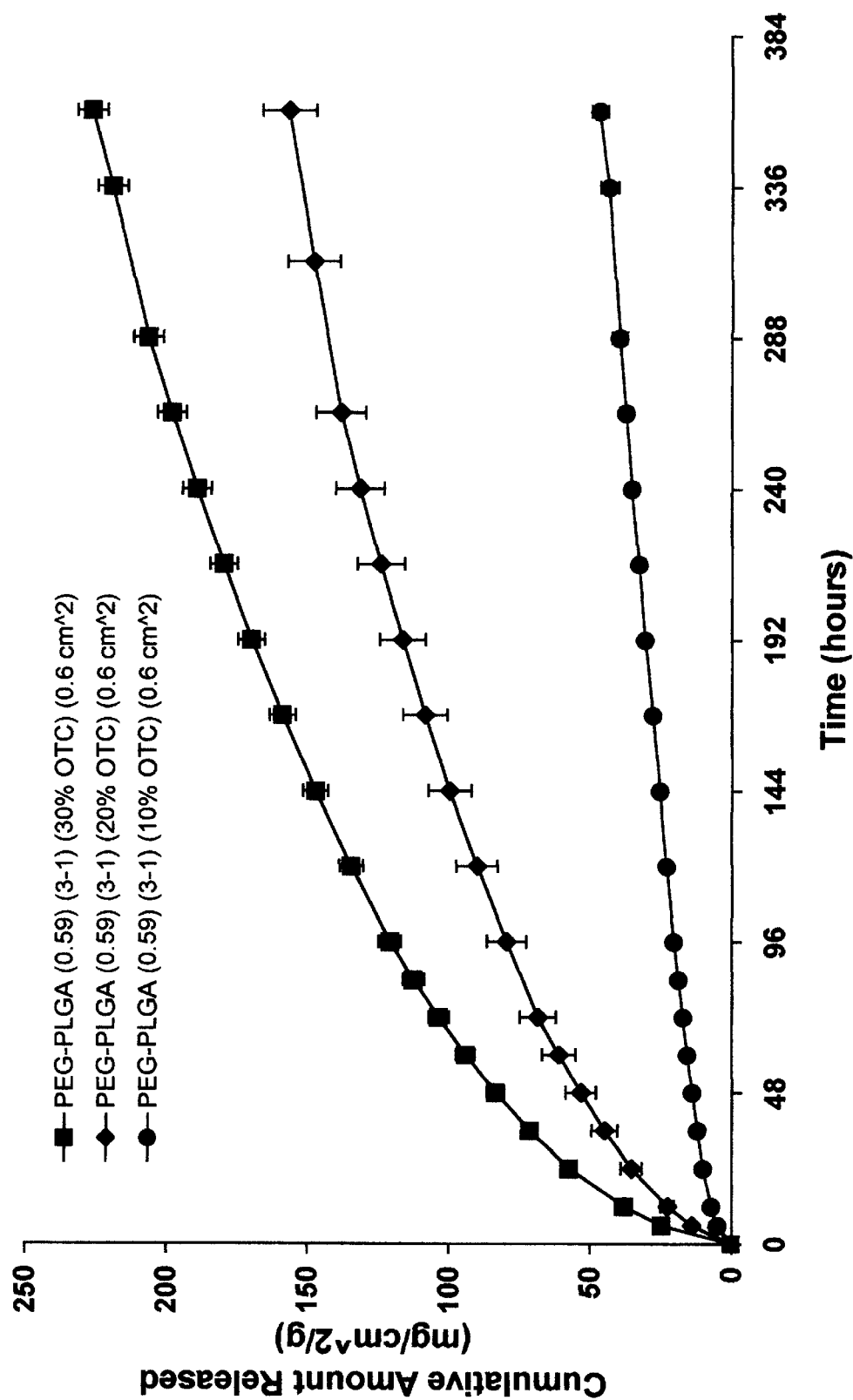
FIG. 6 describes the effect of varying drug loading on oxytetracycline base released from biodegradable gels.

A polymer (25% w/w of 50/50 lactide-co-glycolide copolymer, inherent viscosity of 0.59) was dissolved in a minimum quantity of acetone. Pure polyethylene glycol 400 (PEG 400) was added to the polymer solution. The solution was stirred to yield a uniform mixture. Acetone was evaporated from the mixture by heating at 60–75° C. with constant stirring. The blank formulation was kept in a vacuum oven at 60–75° C. overnight to ensure complete removal of acetone. The resulting formulation obtained was a matrix with a viscous liquid like consistency. Three different concentrations of oxytetracycline base (either 10, 20 or 30% w/w) were added to the blank formulation and mixed thoroughly to ensure uniform distribution of the drug in the formulations. Drug release from the drug-loaded formulations was performed at 37° C. in isotonic phosphate buffer containing sodium sulfite as an antioxidant. FIG. 6 shows the cumulative amount of oxytetracycline released from formulations prepared with the above-mentioned compositions. Increasing the percentage of drug in the formulations from 10 to 30% w/w increased the cumulative amount of drug released at the end of 350 hours. This increase occurred because, at higher drug-loadings, more drug is available on the surface of the formulations for release Moreover, a higher drug concentration gradient between the formulation and the dissolution medium is expected at 30% w/w drug-loading compared to the one at 10% w/w drug loading.

Example 15
Effect of Plasticizer Compositions on Drug Release

Figure 7:
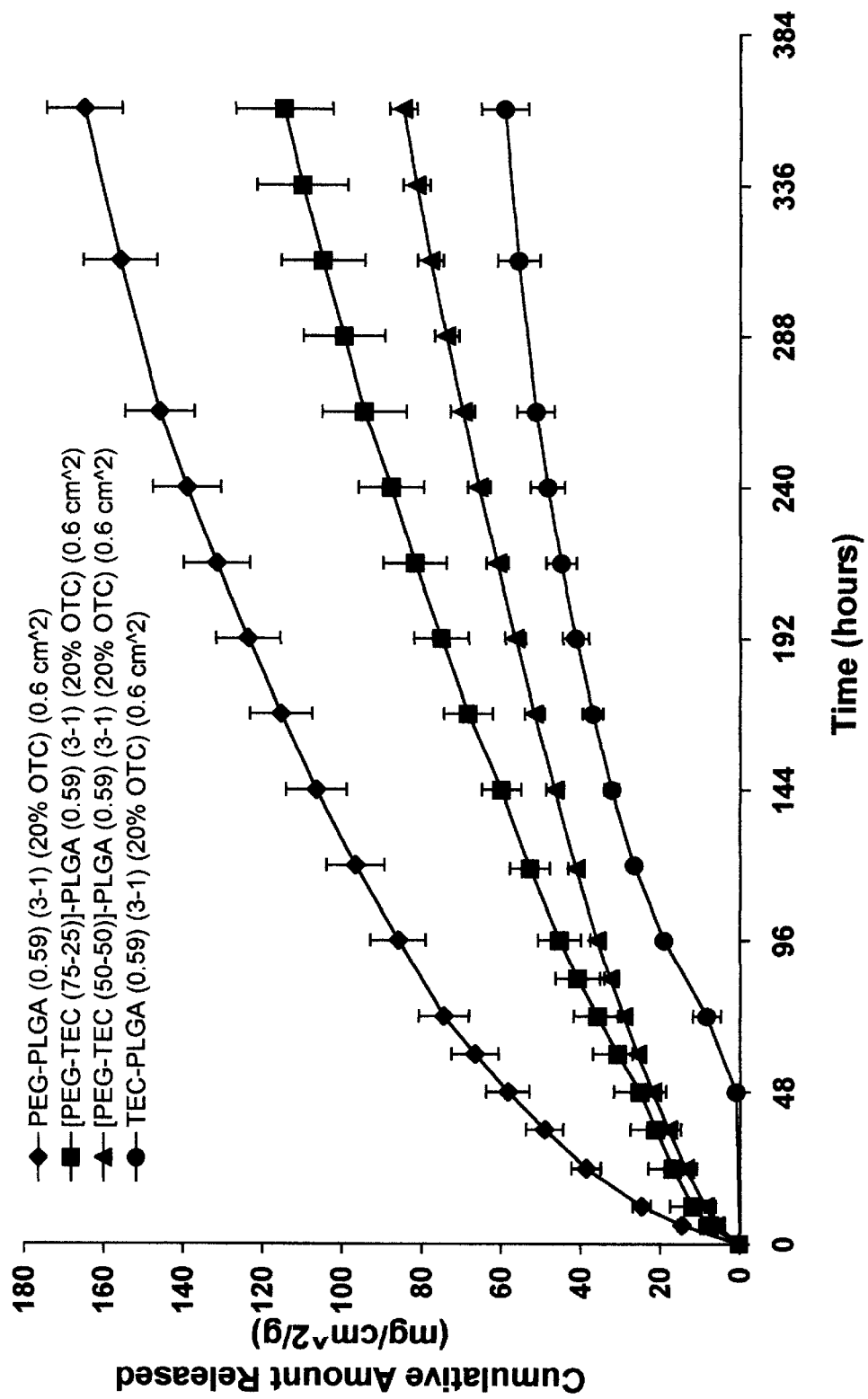
FIG. 7 describes the effect of varying plasticizer composition on oxytetracycline base released from biodegradable gels.

A polymer (25% w/w of 50/50 lactide-co-glycolide copolymer, inherent viscosity of 0.59) was dissolved in a minimum quantity of acetone. Either pure triethyl citrate (TEC), or polyethylene glycol 400 (PEG 400), or blends of PEG 400 and TEC (either 50/50% or 75/25% blends of PEG 400/TEC) was added to the polymer solution. The resulting solutions were stirred to yield uniform mixtures. Acetone was evaporated from the mixtures by heating at 60–75° C. with constant stirring. The blank formulations were kept in a vacuum oven at 60–75° C. overnight to ensure complete removal of acetone. The resulting formulations obtained were matrices with a viscous liquid like consistency. Oxytetracycline base (20% w/w) was added to each blank formulation and mixed thoroughly to ensure uniform distribution of the drug in the formulations. Drug release from the drug-loaded formulations was performed at 37° C. in isotonic phosphate buffer containing sodium sulfite as an antioxidant. FIG. 7 shows the cumulative mount of oxytetracycline released from formulations prepared with the above-mentioned compositions. Increasing the percentage of PEG 400 in the formulations prepared from 0% PEG 400 and 100% TEC to 100% PEG 400 and 0% TEC resulted in faster drug release. This is because PEG 400 is very hydrophilic and is completely miscible in water, whereas, the aqueous solubility of TEC is approximately 6%.

Figure 8:
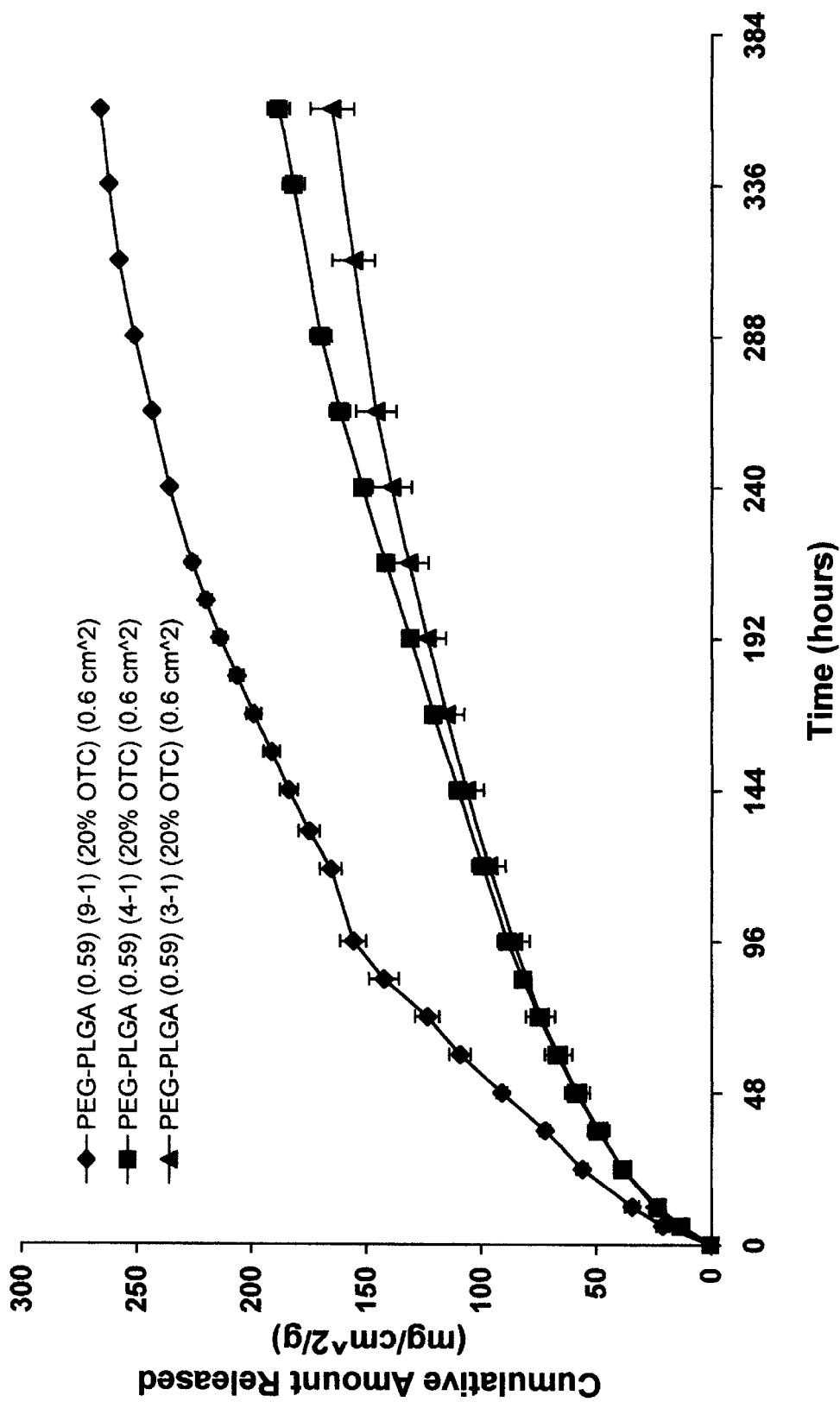
FIG. 8 describes the effect of varying polymer to plasticizer ratios on oxytetracycline base released from biodegradable gels.

Example 16
Effect of Varying Ratios of Polymer and Plasticizer on Drug Release Three different concentrations (10, 20 and 25% w/w) of a polymer (50/50 lactide-co-glycolide copolymer, inherent viscosity of 0.59) were dissolved in a minimum quantity of acetone. Pure PEG 400 (90, 80 or 75%) was added to the polymer solutions. The solutions were stirred to yield uniform mixtures. Acetone was evaporated from the mixtures by heating at 60–75° C. with constant stirring. The blank formulations were kept in a vacuum oven at 60–75° C. overnight to ensure complete removal of acetone. The resulting formulations obtained were matrices with varying viscosities or consistency. The formulation with 25% polymer was considerably more viscous than the one with 10% polymer. Oxytetracycline base (20% w/w) was added to each blank formulation and mixed thoroughly to ensure uniform distribution of the drug in the formulations. Drug release from the drug-loaded formulations was performed at 37° C. in isotonic phosphate buffer containing sodium sulfite as an antioxidant. FIG. 8 shows the cumulative amount of oxytetracycline released from formulations prepared with the above-mentioned compositions. It is evident from the figure that decreasing the percentage of polymer in the formulations from 25% to 10% dramatically increased the drug release. This is because a decrease in polymer concentration from 25% to 10% and a corresponding increase in the plasticizer concentration from 75% to 90% resulted in a decrease in the glass transition temperature, viscosity and an increase in polymer chain mobility of the formulations. Hence, the formulation with 10% polymer offered considerably less resistance for drug diffusion through the matrix compared to the one prepared with 25% polymer.

Example 17
Effect of Varying Plasticizer Hydrophilicity on Drug Release

Figure 9:
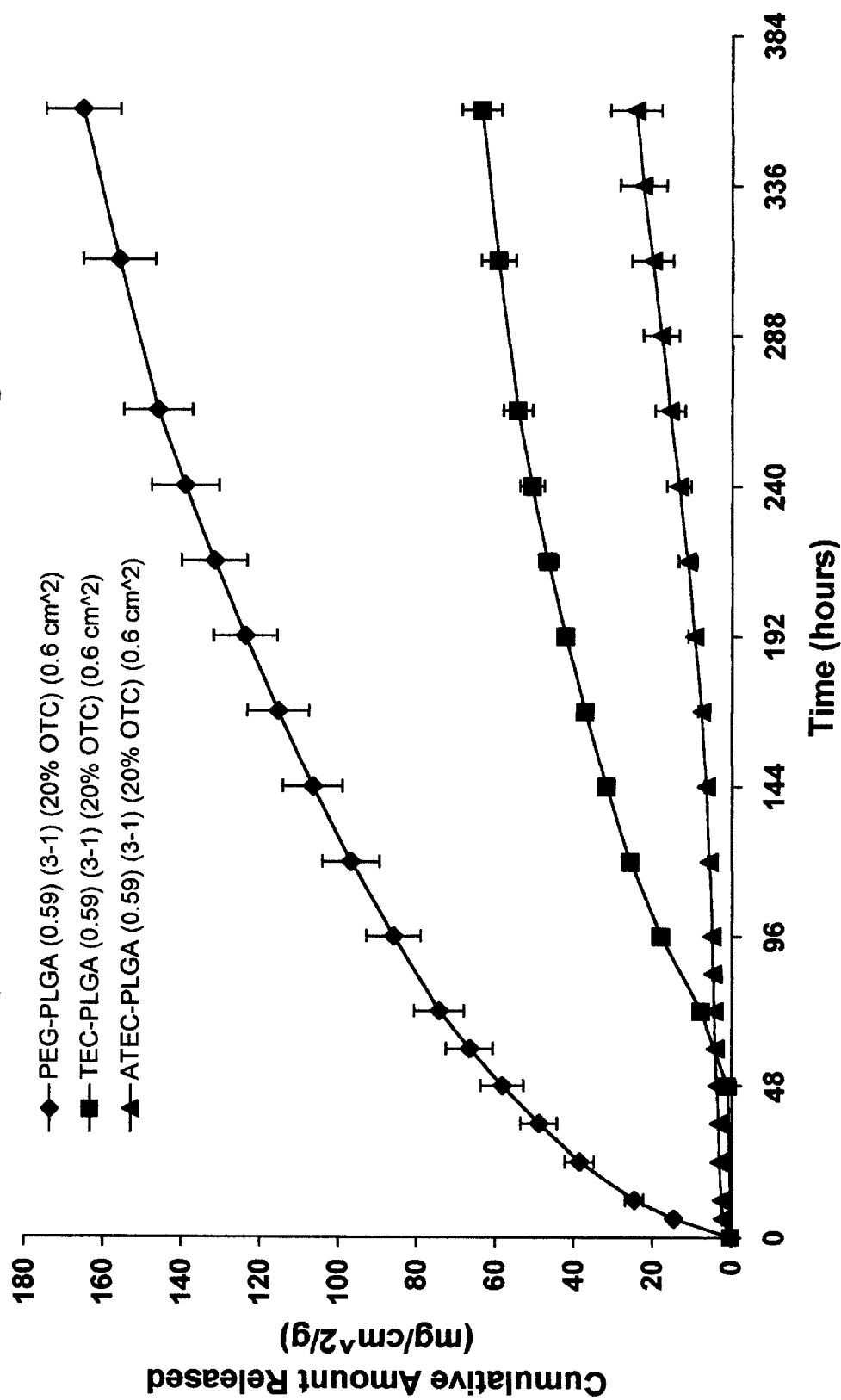
FIG. 9 describes the effect of hydrophilicity of plasticizer on oxytetracycline base released from biodegradable gels.

A polymer (25% w/w of 50/50 lactide-co-glycolide copolymer, inherent viscosity of 0.59) was dissolved in a minimum quantity of acetone. Either pure polyethylene glycol 400, triethyl citrate (TEC) or acetyl triethyl citrate (ATEC) was added to the polymer solution. The resulting solutions were stirred to yield uniform mixtures. Acetone was evaporated from the mixtures by heating at 60–75° C. with constant stirring. The blank formulations were kept in a vacuum oven at 60–75° C. overnight to ensure complete removal of acetone. The resulting formulations obtained were matrices with a viscous liquid like consistency. Oxytetracycline base (20% w/w) was added to each blank formulation and mixed thoroughly to ensure uniform distribution of the drug in the formulations. Drug release from the drug-loaded formulations was performed at 37° C. in isotonic phosphate buffer containing sodium sulfite as an antioxidant. FIG. 9 shows the cumulative amount of oxytetracycline released from formulations prepared with the above-mentioned compositions. It is evident from the figure that drug release was fastest from formulations prepared with PEG 400, and slowest from those prepared with ATEC. Intermediate drug release was observed from formulations prepared from TEC. This is because PEG 400 is completely miscible with water, whereas, the solubility of TEC in water is approximately 6% and ATEC is almost insoluble in water with an aqueus solubility of less than 0.1%.

Figure 10:
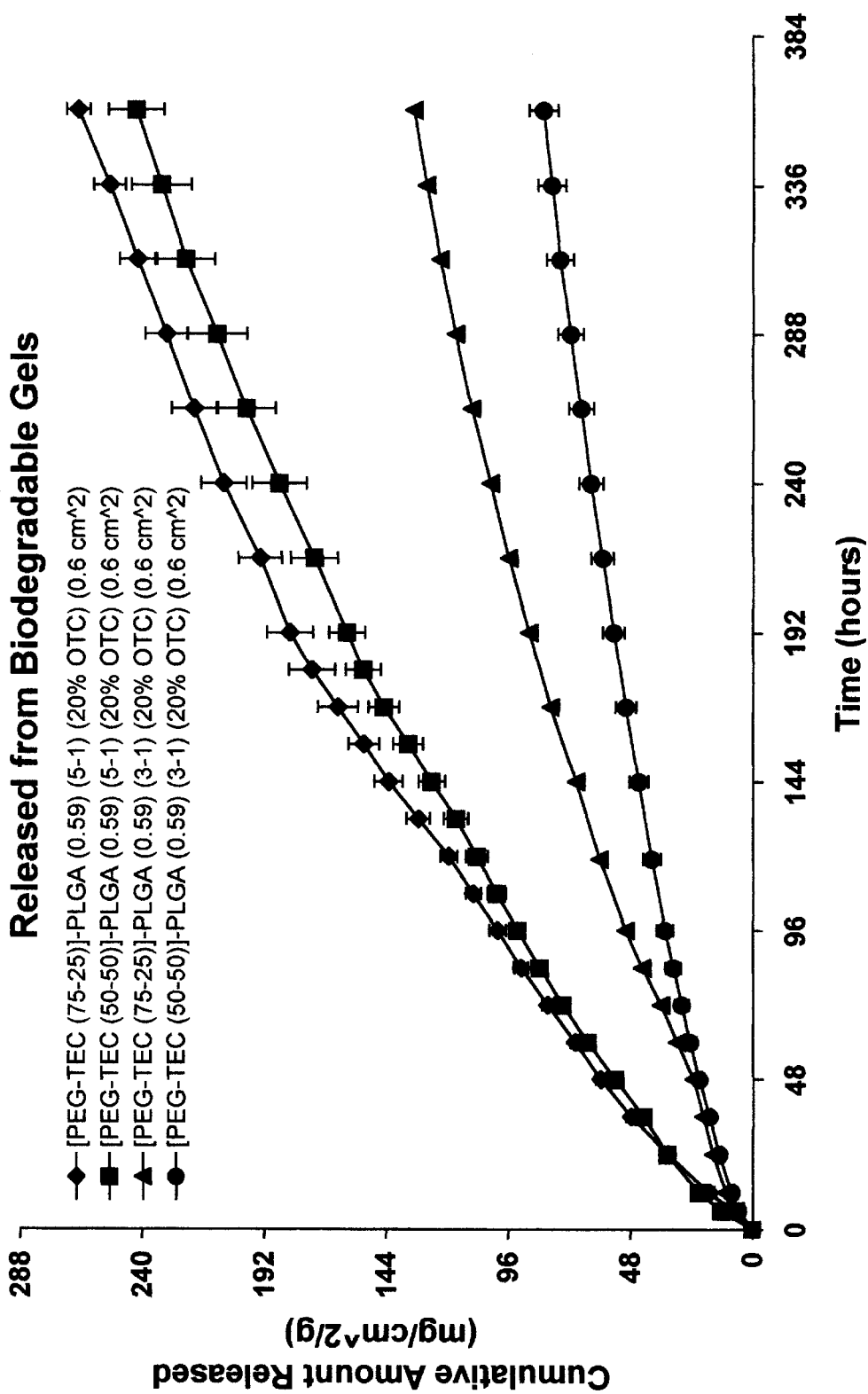
FIG. 10 describes the effect of varying polymer to plasticizer ratios and plasticizer compositions on oxytetracycline base released from biodegradable gels.

Example 18
Effect of Varying Polymer to Plasticizer Ratios and Plasticizer Compositions on Drug Release Blank formulations were prepared by dissolving either 16.67% w/w or 25% w/w of 50/50 polylactide-co-glycolide copolymer (inherent viscosity of 0.59) and either 50/50% or 75/25% blends of PEG 400 and TEC in a minimum quantity of acetone. The resulting solutions were stirred to yield uniform mixtures. Acetone was evaporated from the mixtures by heating at 60–75° C. with constant stirring. The blank formulations were kept in a vacuum oven at 60–75° C. overnight to ensure complete removal of acetone. The resulting formulations obtained were matrices with a viscous liquid like consistency. Oxytetracycline base (20% w/w) was added to each blank formulation and mixed thoroughly to ensure uniform distribution of the drug in the formulations. Drug release from the drug-loaded formulations was performed at 37° C. in isotonic phosphate buffer containing sodium sulfite as an antioxidant. FIG. 10 shows the cumulative amount of oxytetracycline released from formulations prepared with the above-mentioned compositions. It is evident from the figure that faster drug release was observed from formulations prepared with a 16.67% polymer and 83.3% of plasticizer blends of varying compositions polymer to plasticizer ratio of 1:5) compared to those prepared from formulations with polymer to plasticizer ratios of 1:3 (i.e. 33.3% polymer and 66.7% plasticizer). This is because increasing the polymer concentration in the formulations from 16.67% to 33.3% increased the viscosity of the formulations and decreased the drug diffusion from the formulations. Moreover, a comparison of drug released from formulations with similar polymer to plasticizer ratios but varying plasticizer compositions revealed that drug release was considerably faster from formulations prepared with blends of 75% PEG 400 and 25% TEC compared to those prepared from 50/50% blend of PEG 400/TEC. This is because the PEG 400 is completely miscible in water, whereas, the aqueous solubility of TEC in water is approximately 6%).

Example 19
Effect of Varying Polymer Inherent Viscosities on Drug Release

Figure 11:
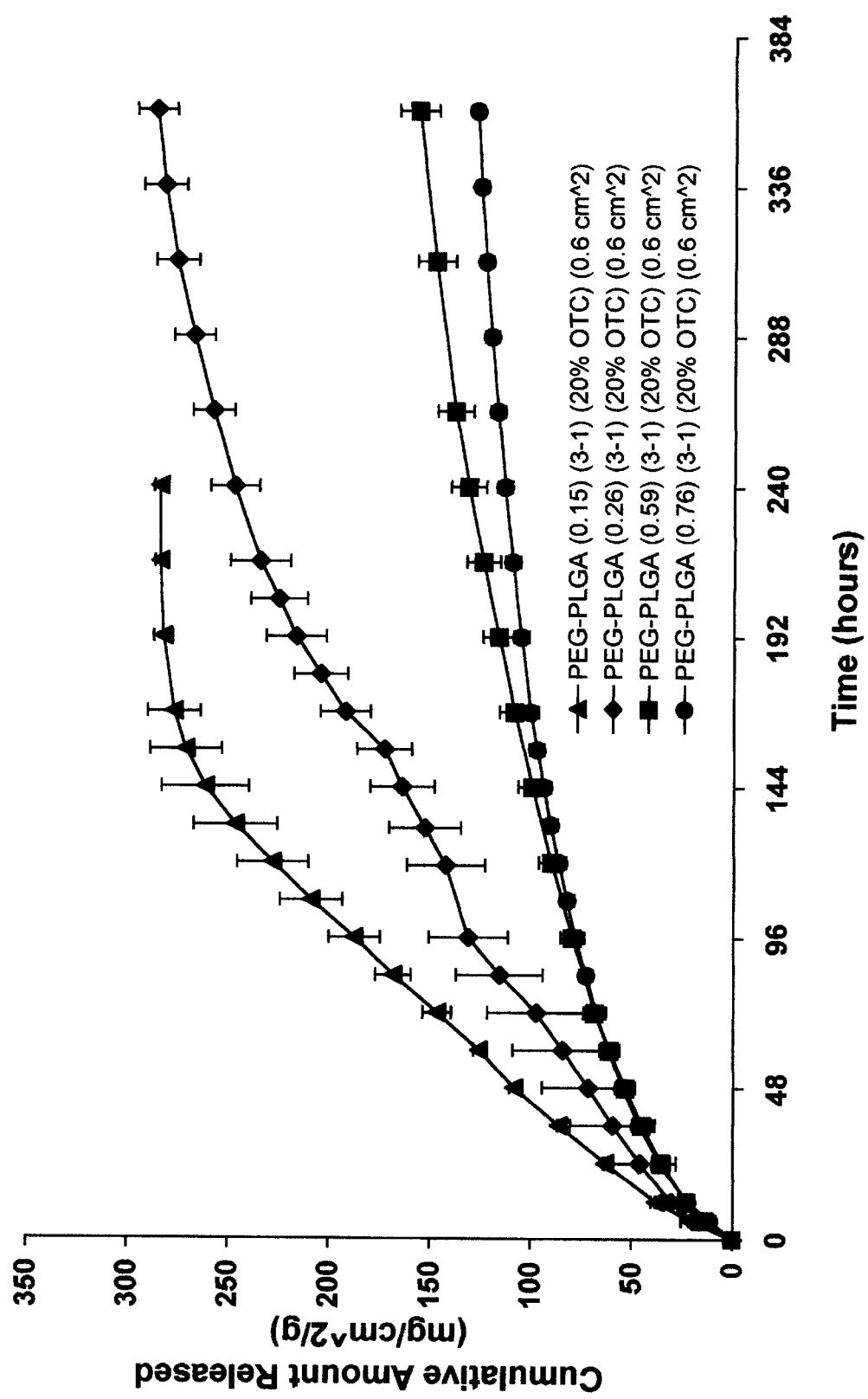
FIG. 11 describes the effect of varying polymer molecular weights on oxytetracycline base released from biodegradable gels.

Four different inherent viscosities (i.v.=0.15, 0.26, 0.59 and 0.76) of a polymer (50/50 lactide-co-glycolide copolymer) were dissolved in a minimum quantity of acetone. Pure PEG 400 was added to the polymer solutions. The solutions were stirred to yield uniform mixtures. Acetone was evaporated from the mixtures by heating at 60–75° C. with constant stirring. The blank formulations were kept in a vacuum oven at 60–75° C. overnight to ensure complete removal of acetone. The resulting formulations obtained were matrices with varying viscosities or consistency. The formulation prepared with the polymer of inherent viscosity of 0.76 was considerably more viscous than the one prepared with the polymer of inherent viscosity of 0.15. Oxytetracycline base (20% w/w) was added to each blank formulation and mixed thoroughly to ensure uniform distribution of the drug in the formulations. Drug release from the drug-loaded formulations was performed at 37° C. in isotonic phosphate buffer containing sodium sulfite as an antioxidant. FIG. 11 shows the cumulative amount of oxytetracycline released from formulations prepared with the above-mentioned compositions. It is evident from the figure that decreasing the inherent viscosity of polymer from 0.76 to 0.15 dramatically increased the drug release. This is because a decrease in polymer inherent viscosity resulted in a dramatic decrease in the viscosity of the formulation and a corresponding decease in resistance to drug diffusion from the matrix.

Example 20
Effect of Varying Drug Solubility on Drug Release

Figure 12:
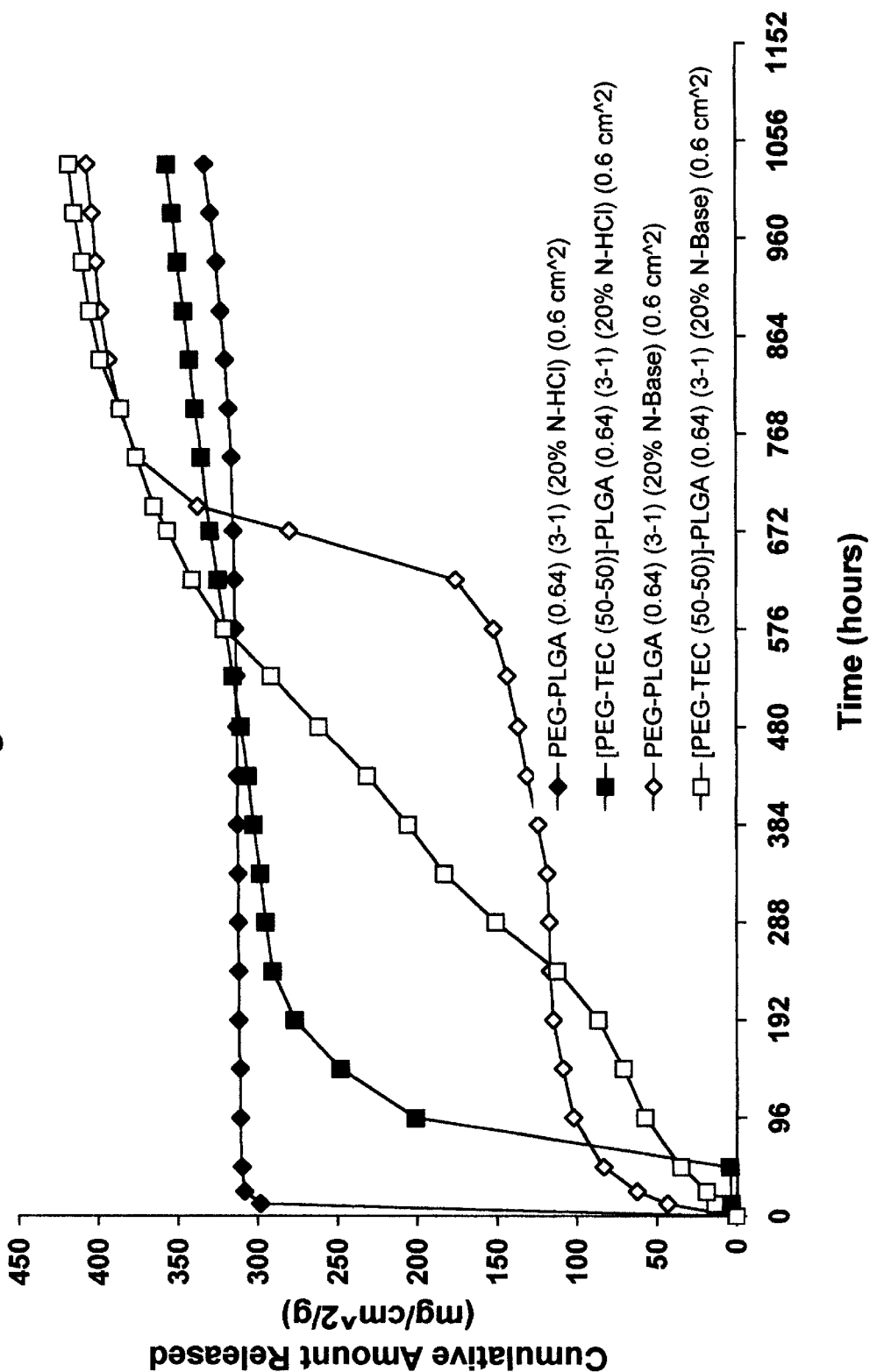
FIG. 12 describes the effect of varying drug solubility on drug released from biodegradable gels.

Blank formulations was prepared by dissolving 25% of a polymer (50/50 lactide-co-glycolide copolymer, inherent viscosity of 0.64) and pure PEG 400 or 50/50% blends of PEG 400 and TEC in a minimum quantity of acetone. The solutions were stirred to yield a uniform mixture. Acetone was evaporated from the mixtures by heating at 60–75° C. with constant stirring. The blank formulations were kept in a vacuum oven at 60–75° C. overnight to ensure complete removal of acetone. The resulting formulations obtained were a matrix with viscous liquid-like consistency. Either hydrated naltrexone base (20% w/w) or naltrexone hydrochloride (20% w/w) was added to the blank formulations and mixed thoroughly to ensure uniform distribution of the drugs in the formulations. Drug release from the drug-loaded formulations was performed at 37° C. in isotonic phosphate buffer. FIG. 12 shows the cumulative amount of either hydrated naltrexone base or naltrexone hydrochloride released from formulations prepared with the above-mentioned compostions. The release of naltrexone hydrochloride is considerably faster from formulations prepared with both pure PEG 400 and 50/50% blends of PEG 400 and TEC than the release of the hydrated naltrexone base from similar formulations. This is because the solubility of the naltrexone hydrochloride in the dissolution buffer is much greater than that of the hydrated naltrexone base.

Figure 13:
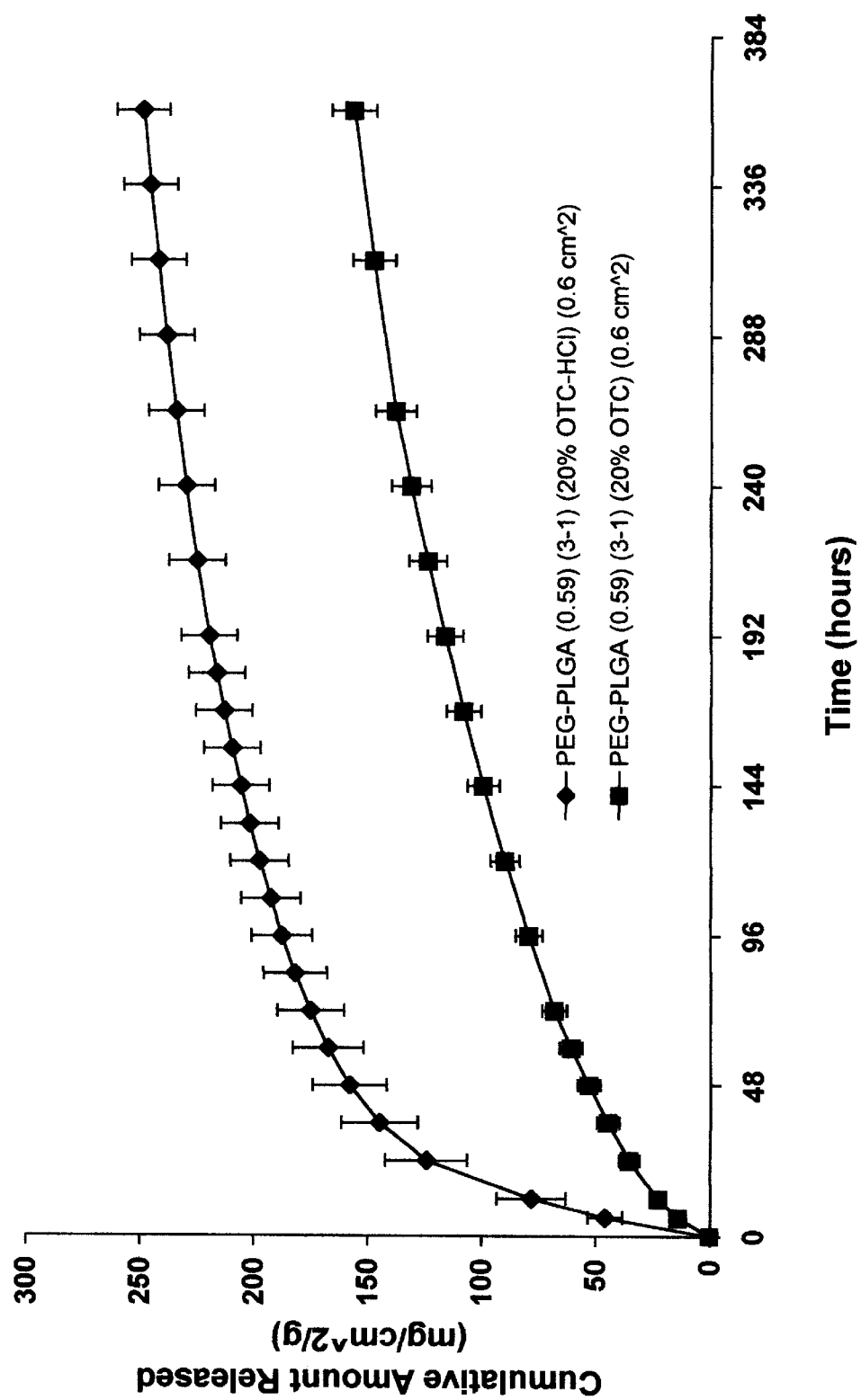
FIG. 13 describes the effect of varying hydrophilicity of drug on oxytetracycline released from biodegradable gels.

A similar drug release study was performed with formulations containing either 20% oxytetracycline hydrochloride or 20% oxytetracycline base. The blank formulations were prepared by dissolving 25% of a polymer (50/50 lactide-co-glycolide copolymer, inherent viscosity of 0.59) and 75% of pure PEG 400 in a minimum quantity of acetone. The solutions were stirred to yield a uniform mixture. Acetone was evaporated from the mixtures by heating at 60–75° C. with constant stirring. The blank formulations were kept in a vacuum oven at 60–75° C. overnight to ensure complete removal of acetone. The resulting formulations obtained were a matrix with viscous liquid-like consistency. Either 20% oxytetracycline hydrochloride or 20% oxytetracycline base was added to the resulting formulations and mixed thoroughly to ensure uniform drug distribution. Drug release from the drug-loaded formulations was performed at 37° C. in isotonic phosphate buffer containing sodium sulfite as an antioxidant. FIG. 13 shows the cumulative amount of oxytetracycline released from formulations prepared with the above-mentioned compositions. It is evident from the figure that the release of oxytetracycline hydrochloride is considerably faster than the release of oxytetracycline base from similar formulations. This is because of the greater aqueous solubility of the hydrochloride salt than the base.

Example 21

Biodegradable delivery systems could be prepared by the procedures shown in Examples 1–20. Instead of adding a single biologically active agent, a combination of two or more biologically active agents could be incoprporated together in the said delivery system. Examples of some of the combinations of the biologically active agents include levonorgestrel and ethinyl estradiol, trimethoprim and sulfamethoxazole, trimetrexate and leucovorin, isoniazid, rifampin and ethambutol, dapsone and rifampicin, erythromycin and rifampicin, clotrimazole and nystatin, amphotericin B and flucytosine, hydrochlorothiazide and amiloride, hydrochlorothiazide and spironolactone, hydrochlorothiazide and captopril, polythiazide and reserpine. Moreover, instead of adding a single plasticizer, a combination of two or more plasticizers could be added to obtain a formulation with the desired consistency and hydrophilicity or hydrophobicity. An example of a combination of plasticizer is acetyl triacetyl citrate (ATEC), n-methyl pyrrolidone (NMP) and a vegetable oil such as sesame oil, olive oil, safflower oil, sunflower oil, cotton seed oil or almond oil.

What is claimed is:

1. A biodegradable delivery system comprising:
   (a) at least one biodegradable polymer, said polymer selected from the group consisting of polyesters, polyorthoesters, polylactides, polyglycolides, polycaprolactones, polyhydroxybutyrates, polyhydroxyvalerates, polyamides and polyanhydrides; and
   (b) at least two plasticizers, one of said plasticizers being hydrophilic and the other of said plasticizers being hydrophobic; and
   (c) at least one biologically active substance.

2. The biodegradable delivery system of claim I wherein each of said plasticizers is selected from the group consisting of citrates, phthalates, sebacates, glycol ethers, diethylene glycol monoethyl ether, polyethylene glycols, PEG-8-glyceryl caprylate-caprate, N-methylpyrrolidone, dipropylene glycol methyl ether acetate, propylene carbonate, gamma butyrolactone, vegetable oils obtained from seeds, flowers, fruits, leaves, or stem of a plant or tree, cotton seed oil, soy bean oil, almond oil, sunflower oil, peanut oil, sesame oil, glyceryl esters of acids and fatty acids, polyethylene glycol esters of acids and fatty acids, glyceryl triacetate, 2-pyrrolidone, propylene glycol, glycerol and sorbitol.

3. The biodegradable delivery system of claim 1 wherein said biologically active substance is selected from the group consisting of steroids, hormones, antipsychotic agents, agents that act on the central nervous system, fertility regulating agents, antibodies, antigens, anesthetics, analgesics, antibiotics, antiviral agents, antineoplastic agents, antifungal agents, cavity- and infection-preventing agents, cardiovascular agents, antiinflammatory agents, vasodilators, bronchiodilators, alkaloids, peptides, proteins, growth promoting agents, deoxyribonucleic acid, whole viable cells and cell-lines, and biological tissues.

4. A biodegradable delivery system comprising:
(a) at least two biodegradable polymers, each of said polymers selected from the group consisting of polyesters, polyorthoesters, polylactides, polyglycolides, polycaprolactones, polyhydroxybutyrates, polyhydroxyvalerates, polyamides and polyanhydrides; and
(b) at least two plasticizers, one of said plasticizers being hydrophilic and the other of said plasticizers being hydrophobic; and
(c) at least one biologically active substance.

5. A method of preparing a biodegradable delivery system comprising the steps of:
(a) selecting at least one biodegradable polymer, said polymer selected from polyesters, polyorthoesters, polylactides, polyglycolides, polycaprolactones, polyhydroxybutyrates, polyhydroxyvalerates, polyamides and polyanhydrides;
(b) dissolving said polymer in at least one volatile solvent to form a solution;
(c) adding at least two plasticizers, one of said plasticizers being hydrophilic and the other of said plasticizers being hydrophobic, to said solution of step (b);
(d) evaporating said solvent from the solution of step (c); and
(e) adding at least one biologically active substance to the product of step (d) wherein the said biodegradable delivery system is loaded with at least one biologically active substance.

6. The method of claim 5 wherein said volatile solvent is selected from a group consisting of acetone, methyl acetate, ethyl acetate, chloroform, dichloromethane, methyl ethyl ketone, hexafluroisopropanol, tetrahydrofuran and hexafluroacetone sesquihydrate.

7. The method of claim 5 wherein each of said plasticizers is selected from the group consisting of citrates, phthalates, sebacates, glycol ethers, diethylene glycol monoethyl ether, polyethylene glycols, PEG-8-glyceryl caprylate-caprate, N-methylpyrrolidone, dipropylene glycol methyl ether acetate, propylene carbonate, gamma butyrolactone, vegetable oils obtained from seeds, flowers, fruits, leaves, or stem of a plant or tree, cotton seed oil, soy bean oil, almond oil, sunflower oil, peanut oil, sesame oil, glyceryl esters of acids and fatty acids, polyethylene glycol esters of acids and fatty acids, glyceryl triacetate, 2-pyrrolidone, propylene glycol, glycerol and sorbitol.

8. The method of claim 5 wherein said biologically active substance is selected from the group consisting of steroids, hormones, antipsychotic agents, agents that act on the central nervous system, fertility regulating agents, antibodies, antigens, anesthetics, analgesics, antibiotics, antiviral agents, antineoplastic agents, antifungal agents, cavity- and infection-preventing agents, cardiovascular agents, antiinflammatory agents, vasodilators, bronchiodilators, alkaloids, peptides, proteins, growth promoting agents, deoxyribonucleic acid, whole viable cells and cell-lines, and biological tissues.

9. A method of preparing a biodegradable delivery system comprising the steps of:
(a) selecting at least one biodegradable polymer, said polymer selected from the group consisting of polyesters, polyorthoesters, polylactides, polyglycolides, polycaprolactones, polyhydroxybutyrates, polyhydroxyvalerates, polyamides and polyanhydrides;
(b) dissolving said polymer in at least one volatile solvent to form a solution;
(c) adding at least two plasticizers, one of said plasticizers being hydrophilic and the other of said plasticizers being hydrophobic, to said solution of step (b);
(d) adding at least one biologically active substance to the product of step (c); and
(e) evaporating said solvent from the product of step (d.

10. The method of claim 9 wherein said volatile solvent is selected from a group consisting of acetone, methyl acetate, ethyl acetate, chloroform, dichloromethane, methyl ethyl ketone, hexafluroisopropanol, tetrahydrofuran and hexafluroacetone sesquihydrate.

11. The method of claim 9 wherein each of said plasticizers is selected from the group consisting of citrates, phthalates, sebacates, glycol ethers, diethylene glycol monoethyl ether, polyethylene glycols, PEG-8-glyceryl caprylate-caprate, N-methylpyrrolidone, dipropylene glycol methyl ether acetate, propylene carbonate, gamma butyrolactone, vegetable oils obtained from seeds, flowers, fruits, leaves, or stem of a plant or tree, cotton seed oil, soy bean oil, almond oil, sunflower oil, peanut oil, sesame oil, glyceryl esters of acids and fatty acids, polyethylene glycol esters of acids and fatty acids, glyceryl triacetate, 2-pyrrolidone, propylene glycol, glycerol and sorbitol.

12. The method of claim 9 wherein said biologically active substance is selected from the group consisting of steroids, hormones, antipsychotic agents, agents that act on the central nervous system, fertility regulating agents, antibodies, antigens, anesthetics, analgesics, antibiotics, antiviral agents, antineoplastic agents, antifungal agents, cavity- and infection-preventing agents, cardiovascular agents, antiinflammatory agents, vasodilators, bronchiodilators, alkaloids, peptides, proteins, growth promoting agents, deoxyribonucleic acid, whole viable cells and cell-lines, and biological tissues.

13. The biodegradable delivery system of claim 3 wherein said growth promoting agents are calcium phosphates or hydroxyapatites.

14. The method of claim 8 wherein said growth promoting agents are calcium phosphates or hydroxyapatites.

15. The method of claim 12 wherein said growth promoting agents are calcium phosphates or hydroxyapatites.

16. The biodegradable delivery system of claim 4 wherein said plasticizers are selected from the group consisting of citrates, phthalates, sebacates, glycol ethers, diethylene glycol monoethyl ether, polyethylene glycols, PEG-8-glyceryl caprylate-caprate, N-methylpyrrolidone, dipropylene glycol methyl ether acetate, propylene carbonate, gamma butyrolactone, vegetable oils obtained from seeds, flowers, fruits, leaves, or stem of a plant or tree, cotton seed oil, soy bean oil, almond oil, sunflower oil, peanut oil, sesame oil, glyceryl esters of acids and fatty acids, polyethylene glycol esters of acids and fatty acids, glyceryl triacetate, 2-pyrrolidone, propylene glycol, glycerol and sorbitol.

17. The biodegradable delivery system of claim 1 comprising at least two biologically active substances.

18. The biodegradable delivery system of claim 4 comprising at least two biologically active substances.

19. The method of claim 5 comprising adding at least two biologically active substances to the product of step (d).

20. The method of claim 9 comprising adding at least two biologically active substances to the product of step (c).

21. The biodegradable delivery system of claim 4 wherein said biologically active substance is selected from the group consisting of steroids, hormones, antipsychotic agents, agents that act on the central nervous system, fertility regulating agents, antibodies, antigens, anesthetics, analgesics, antibiotics, antiviral agents, antineoplastic agents, antifungal agents, cavity- and infection-preventing agents, cardiovascular agents, antiinflammatory agents, vasodilators, bronchiodilators, alkaloids, peptides, proteins, growth promoting agents, deoxyribonucleic acid, whole viable cells and cell-lines, and biological tissues.

22. The biodegradable delivery system of claim 21 wherein said growth promoting agents are calcium phosphates or hydroxyapatites.

* * * * *